United States Patent [19]

Remy et al.

[11] Patent Number: 5,021,440

[45] Date of Patent: Jun. 4, 1991

[54] IMIDAZOLE COMPOUNDS AND THEIR USE AS TRANSGLUTAMINASE INHIBITORS

[75] Inventors: David C. Remy, North Wales; John J. Baldwin, Gwyneed Valley; David A. Claremon, Audubon; Stella W. King, Lansdale, all of Pa.

[73] Assignee: Merck & Co., Inc., Rahway, N.J.

[21] Appl. No.: 386,646

[22] Filed: Jul. 31, 1989

[51] Int. Cl.$^5$ .................. A61K 31/415; C07D 403/12
[52] U.S. Cl. ..................... 514/381; 514/393; 514/397; 548/251; 548/323; 548/336
[58] Field of Search ........ 548/336, 251, 323; 514/397, 381, 393

[56] References Cited

U.S. PATENT DOCUMENTS 4,188,397 2/1980 Hill ........................................ 548/336
4,218,476 8/1980 Jöensson et al. ................... 514/604
4,265,898 5/1981 Horstmann et al. ................ 514/363

FOREIGN PATENT DOCUMENTS 229496 12/1986 European Pat. Off. .

OTHER PUBLICATIONS

Bender et al., C.A., vol. 110 (11), 88621b, Feb. 25, 1988. Chemical Abstracts Service.
Bender et al., C.A., vol. 107 (19), 176041f, Jul. 22, 1987. Chemical Abstracts Service.
Kister et al., Can. J. Chem. 57,813 (1979).
Kister et al., Can. J. Chem. 57,822 (1979).

*Primary Examiner*—Mary C. Lee
*Assistant Examiner*—Lenora A. Miltenberger
*Attorney, Agent, or Firm*—Alice O. Robertson; Hesna J. Pfeiffer

[57] ABSTRACT

Imidazole compounds including imidazoles and imidazolium salts, and their use as transglutaminase inhibitors are disclosed.

12 Claims, No Drawings ize
IMIDAZOLE COMPOUNDS AND THEIR USE AS TRANSGLUTAMINASE INHIBITORS

BACKGROUND OF THE INVENTION

Transglutaminases, also known as transamidases, are a family of enzymes which catalyze the amide bond formation of the γ-Carboxamide group of peptide glutamine residues with an ε amino group of peptide lysine residues.

A number of disease states have been associated with transglutaminase activity. Thus, for example, in acne lesions, transglutaminase activity in sebaceous follicles has been reported by DeYoung et. al., in J. Investigative Dermatology, 82, 275 (1984). Also. the cornified cell envelope in acne has been reported to be a result of transglutaminase activity by Dalziel et. al., Br. J. Exp. Pathology, 65, 107–115 (1984).

Another dermatological disease, psoriasis, is reported to be associated with excessive transglutaminase activity by Bernard et. al. British Journal of Dermatology, 114, 279 (1986).

Cataracts also have been reported to be associated with elevated transglutaminase activity.

Factor XIIIa is a plasma transglutaminase which is the activated form of Factor XIII also known as fibrinase or fibrin-stabilizine factor. It is essential for normal hemostasis and is responsible for the :ross-linking of fibrin.

While the activity of this enzyme may be desirable and essential under most circumstances, activity under certain other circumstances can be highly undesirable. Thus, excessive thrombosis, that is the formation of clot within a blood vessel, gives rise to thrombotic strokes, deep vein thrombosis, variant angina, myocardial infarction, and other medical conditions which frequently result in necrosis of tissues and oftentimes in death of a patient. Even if death does not occur, thrombotic attacks are accompanied by damage to cells to which circulation has been prevented by thrombi formation. Removal of the thrombi by lysis is essential and the rate of lysis may be critical in ultimate patient recovery.

Lysis may occur normally in hours or days by the action of a proteolytic enzyme, plasmin, which is present in plasma as the inactive precursor plasminogen, and which is activated by plasminogen activators, such as (pro)urokinase, urokinase or tissue plasminogen activator (tPA). Since the occurrence of a thrombotic event calls for rapid remedial action, administration of exogenous tissue plasminogen activator or (pro)urokinase is currently used in thrombolytic or fibrinolytic therapy. However, a still further reduction in lysis time is desirable to minimize cell injury.

Since Factor XIIIa is an enzyme responsible for the final event in the coagulation of blood, lysis and maintaining the lytic state can be facilitated by the presence of a Factor XIIIa inhibitor. Moreover, the presence of a Factor XIIIa inhibitor as in a prophylactic treatment when thrombosis an be anticipated would inhibit hard clot formation. Thus, a Factor XIIIa inhibitor is useful in inhibiting thrombosis, in treating thrombosis when used with a plasminogen activator or anticoagulant and in post fibrinolytic therapy in maintaining the lytic state.

STATEMENT OF THE INVENTION

A novel class of imidazole compounds has been discovered which inhibits transglutaminase activity particularly, Factor XIIIa activity. The invention also embraces compositions and methods for using the imidazole compounds as Factor XIIIa inhibitors in fibrinolytic or thrombolytic therapy. For use as Factor XIIIa inhibitors, the compounds may be used alone or together with agents used in thrombolytic or fibrinolytic therapy such as a plasminogen activator, a platelet aggregation inhibitor or an anticoagulant.

DETAILED DESCRIPTION OF THE INVENTION

The imidazole compounds of the present invention are compounds selected from the group consisting of (A) an imidazole represented by the formula $$\underset{R^2}{\overset{R^3}{\diagdown}}{=}\underset{\underset{R^1}{|}}{\overset{N}{\diagup}}\hspace{-2pt}\diagdown\hspace{-2pt}{-}S{-}CH_2{-}\overset{\overset{O}{\|}}{C}{-}CH_2{-}S{-}W \quad (I)$$

or its acid addition salt, and (B) an imidazolium salt represented by the formula $$\underset{R^2}{\overset{R^3}{\diagdown}}{=}\underset{\underset{R^1 \; X^{\ominus}}{|}}{\overset{\overset{R^4}{|}}{\overset{N^{\oplus}}{\diagup}}}\hspace{-2pt}\diagdown\hspace{-2pt}{-}S{-}CH_2{-}\overset{\overset{O}{\|}}{C}{-}CH_2{-}S{-}W \quad (IIA)$$

(C) an imidazolium salt represented by the formula;

$$\underset{R^2}{\overset{R^3}{\diagdown}}{=}\underset{\underset{R^1 \; X^{\ominus}}{|}}{\overset{\overset{R^4}{|}}{\overset{N^{\oplus}}{\diagup}}}\hspace{-2pt}\diagdown\hspace{-2pt}{-}S{-}CH_2{-}\overset{\overset{O}{\|}}{C}{-}CH_2{-}S{-}\overset{\oplus}{W'} \quad Z^{\ominus} \quad (IIB)$$

In the foregoing and succeeding formulas $R^1$ is lower alkyl or $ArC_nH_{2n}-$ wherein Ar is phenyl, (lower alkyl)phenyl, (lower alkoxy)phenyl or halophenyl and n is 1–3;

$R^2$ is hydrogen, lower alkyl, halo, phenyl or substituted phenyl containing from 1 to 3 substituents selected from lower alkyl, lower alkoxy, halo and hydroxy;

$R^3$ is hydrogen, or when $R^2$ is phenyl or substituted phenyl is optionally the same as $R^2$ $R^2$ and $R^3$ taken together may be alkylene of from 3 to 10 carbon atoms, $R^4$ is lower alkyl or $ArC_nH_{2n}$, wherein Ar is phenyl, (lower alkyl)phenyl, (lower alkoxy)phenyl or halophenyl and n is 1–3: and W is $$-\hspace{-3pt}\diagup\hspace{-10pt}\diagdown\underset{\underset{R^1}{|}}{\overset{N}{\diagdown}}\hspace{-2pt}{=}\hspace{-2pt}\underset{R^2}{\overset{R^3}{\diagup}}$$

where $R^1$, $R^2$, $R^3$ are as previously defined, or

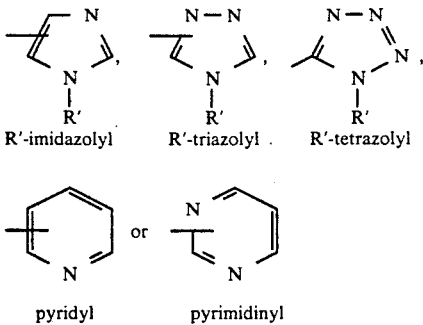

R'-imidazolyl    R'-triazolyl    R'-tetrazolyl pyridyl    pyrimidinyl wherein R' is lower alkyl or $ArC_nH_{2n}-$ wherein Ar is phenyl, (lower alkyl)phenyl, (lower alkoxy)phenyl or halophenyl and n is 1-3;

W' is

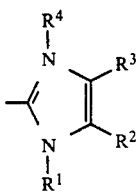

where $R^1$, $R^2$, $R^3$, and $R^4$ are as previously defined, or

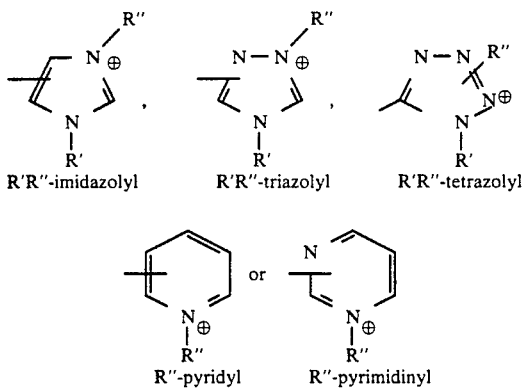

R'R"-imidazolyl    R'R"-triazolyl    R'R"-tetrazolyl

R"-pyridyl    R"-pyrimidinyl wherein R' and R" independently are lower alkyl or $ArC_nH_{2n}$ wherein Ar is phenyl, (lower alkyl)phenyl, (lower alkoxy)phenyl or halophenyl and n is 1-3;

X is a negative radical of a pharmaceutically acceptable salt, and

Z is a negative radial of a pharmaceutically acceptable salt.

By the expressions "lower alkyl" and "lower alkoxy" as employed in the specification and claims are meant radicals having from 1 to 6 carbon atoms.

By the expression "halo" is meant fluoro, chloro bromo or iodo.

Pharmaceutically acceptable salts suitable as acid additon salts as well as providing the anion of the quaternary salts are those from acids such a hydrochloric, hydrobromic, hydroiodic, phosphroic, sulfuric, trifluoroacetic, trichloroacetic, oxalic, maleic, pyruvic, malonic, succinic, citric, mandelic, benzoic, cinnami:, methanesulfonic, ethanesulfonic, and the like, and include other acids related to the pharmaceutically acceptable salts listed in Journal of Pharmaceutical Science, 66, 2 (1977) and incorporated herein by reference.

The preferred compounds are the quaternary salts (IIA) and (IIB). Compounds represented by formula (I) are useful additionally as intermediates in some of the methods for the preparation of the preferred quaternary salts.

The compounds, both those which are acid addition salts of the compounds represented by formula (I) and those quaternary salts represented by formula (IIA) or (IIB) are solids soluble in polar solvents such as methanol, ethanol, isopropanol and the like. The imidazoles of formula (I) are soluble in non-polar solvents such as ethyl acetate, methylene chloride, diethylene chloride carbon tetrachloride, and the like.

The compounds of the present invention are useful as transglutaminase inhibitors, particularly as Factor XIIIa inhibitors, and may be employed in thrombolytic therapy. In such use, it is administered to a thrombotic patient susceptible to thrombotic: attack either alone or in combination.

Preferably, it is employed together with a plasminogen activator, an enzyme which converts plasminogen to plasmin to increase the rate and extent of lysis. Suitable activators include tissue plasminogen activator (tPA), prourokinase (single chain urokinase), urokinase (dual chain urokinase), streptokinase and eminase (European patent application 028,489). The Plasminogen activators may c be those isolated from natural sources or produced by recombinant technology and include the genetically engineered variants thereof.

Also, it may be employed together with platelet aggregation inhibitors. Platelet aggregation inhibitors may be drugs, naturally occurring proteins or peptides or may be modified or semi synthetic proteins or peptides.. Established drugs which are platelet aggregation inhibitors include aspirin and dipyridamole Proteins or polypeptides which are platelet aggregation inhibitors have a certain peptide sequence, most frequently Arg-Gly-Asp (arginine-glysine aspartic acid). Some classes of natural proteins having this property are fibrinogen receptor antagonists, thromboxane receptor antagonists, thromboxane synthesis inhibitors, collagen receptor antagonists and thrombin inhibitors. Among especially useful polypeptides are those designated "Echistatin" and "Bitistatin" and having the amino acid sequence X-Cys-R-R-R-Arg-Gly-Asp-R-R-R-R-R-Cys-Y where X is H or an amino acid, Y in OH or an amino acid and each R independently is an amino acid described and claimed in copending applications Ser. No. 184,649, filed Apr. 22, 1988; Ser. No. 303,757, filed Feb. 1, 1989; and Ser. No. 307,642 filed Feb. 7, 1989, all in the names of P.A. Friedman, et al., the teachings of which are incorporated by reference.

Additionally, the imidazole compounds may be employed for continued therapy after initial relief from thrombotic: attack thereby providing a more complete lysis and minimizing complications from reocclusion. Moreover, the imidazole compounds may be employed in post thrombosis therapy together with anticoagulants such as heparin and coumarin drugs.

The preferred compounds for use as transglutaminase inhibitors are the quaternary imidazolium salts.

The compounds of the present invention which are imidazoles may have additional utility as intermediates in one method of preparation of the preferred imidazolium salts.

The compounds of the present invention may be prepared in one of several ways, depending in part on whether a neutral imidazole (I) or a quarternary salt is desired, and if the former, whether it is a symmetrical imidazole having two identical imidazole nuclei or an asymmetrical compound with the second nucleus being a different imidazole nucleus or another heteroaryl nucleus, and if the latter, whether a mono (IIA) or di (IIB) salt is desired. When the expression "heteroaryl" is employed, it refers to either the same imidazole nucleus or a nucleus derived from a different nitrogen heterocycle as represented by W.

When the imidazole of formula (I) is a symmetrical compound as seen in Formula I, two molar proportions of the appropriate imidazole compound, i.e., mercapto-imidazole, may be caused to react with a molar proportion of 1,3-dichloroacetone in the Presence of a tertiary amine (3° amine).

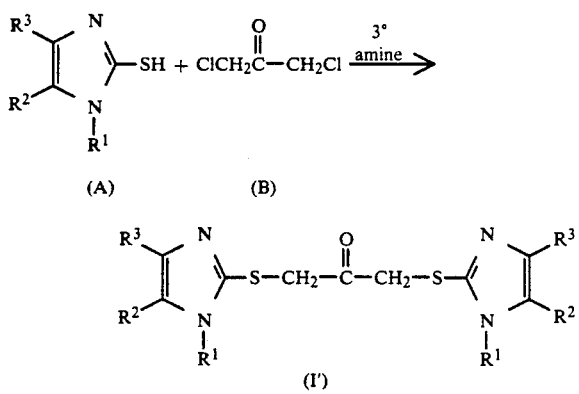

A slight molar excess of a tertiary amine, based on the imidazole, is employed to neutralize the hydrogen chloride formed in the reaction. Suitable tertiary amines are triethylamine, trimethylamine, pyridine, :ollidines, picolines and the like.

The reaction is carried out in solution, initially with cooling and then at ambient temperature to produce the desired imidazole (I). Suitable solvents are acetone, methyl ethyl ketone, ethyl acetate, toluene and the like.

In carrying out the reaction, a solution of 1,3-dichloroacetone is added dropwise with stirring to a solution of the mercaptoimidazole and tertiary amine in an ice bath. After completion of the addition, stirring is continued for several hours with cooling and thereafter at ambient temperature for several days, up to about a week. As a result of these operations, the imidazole (Compound I') forms in the reaction mixture and is accompanied by the formation of the ammonium salt of the tertiary amine which precipitates in the reaction mixture. The latter is removed by filtration and the filtrate subjected to reduced pressure to remove the solvent and recover the imidazole as residue. The latter may be purified by conventional procedures.

The acid addition salts may be prepared in a conventional manner such as by intimately mixing the imidazole and desired acid, preferably in a minimal amount of polar solvent such as ethanol or by other conventional procedures.

The imidazolium salt (IIA Ar IIB) may be prepared from the imidazole compound by contacting the compound with a quaternizing agent such as methyl iodide or methyl trifluoromethanesulfonate in an inert solvent such as methylene chloride, acetone or methyl ethyl ketone. If one mole of quaternizing agent is employed, a mono imidazolium salt may be obtained. If two moles of quaternizing agent is employed a bis salt may be obtained.

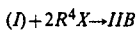

In carrying out the reaction, the quaternizing agent is added with stirring to a solution of the imidazole (I) whereupon the imidazolium salt precipitates. After completion of the precipitation the latter is recovered by filtration and purified, if desired, by conventional procedures.

If the bis salt is desired, a similar procedure may be employed with twice the amount of the quaternizing agent. However, the bis imidazolium salt is preferably obtained by another method. In such method, two moles of the appropriate imidazolinethione is caused to react with 1,3-dichloroacetone.

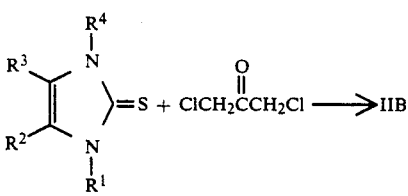

A solvent such as acetone Or methyl ethyl ketone is employed. The time for reaction may be several hours to overnight at room temperature.

In carrying out the reaction, the 1,3-dichloroacetone is added with stirring to a solution of the appropriate imidazoline-thione in a solvent and the mixture stirred at room temperature for time sufficient to complete the reaction with the formation of the desired bis-imidazolium salt. The salt is recovered and purified, if desired, by conventional procedures.

In addition, it may be desired to convert from one salt to another. In such case, an ion exchange column may be prepared and charged with the desired anion employing conventional procedures. Thereafter, a solution of the salt is placed on the column, eluted with appropriate agent and recovered by conventional procedures. Aqueous alcohol solutions are suitable solvents for such exchanges.

When an imidazole compound is desired which is asymmetrical i.e. W is a different imidazole or a different heteroaryl group, one molar proportion of an appropriate imidazole compound may be caused to react with a molar excess of 1,3-dichloroacetone in the presence of a tertiary amine to obtain a 2-chloro acetonylimidazole compound which is thereafter caused to react with an alkali metal salt of a mercaptoheteroaryl compound:

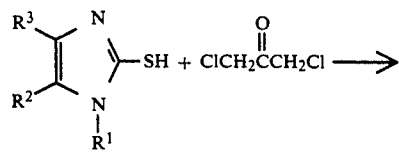

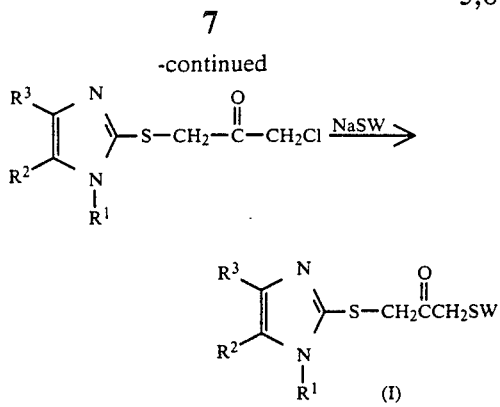

The conditions for reaction except for the stepwise procedure and the use of excess chloroacetone is similar to that for the symmetrical imidazoles. The imidazole compound thus obtained, may be converted to an imidazolium salt in a manner similar to that to be employed for the symmetrical imidazole. However, if the imidazolium salt or the bis-salt is desired, it is preferable to employ a method which produces an imidazolium salt directly as hereinafter described.

In such a procedure, the appropriate imidazolinethione is caused to react with 1,3-dichloroacetone to obtain initially a 2-(ω-chloroacetonyl-thio)imidazolium chloride which then may be caused to react with the sodium salt of the mercaptoheteroaryl compound (NaSW):

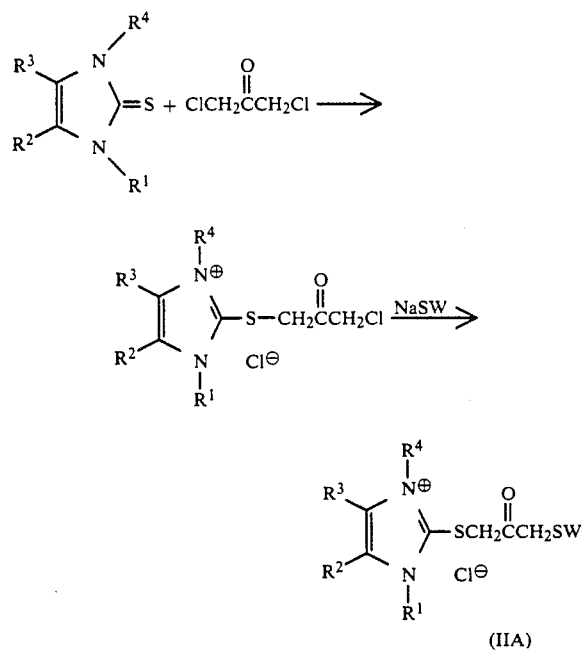

In the first step, substantially equimolar proportions of the imidazolinethione and 1,3-dichloroacetone are employed in a solvent such as acetone or methyl ethyl ketone at ambient temperature for from a few hours to several days. In carrying out the reaction, a solution of the appropriate 1,3-dialkyl- imidazolin-2-thione is added dropwise with stirring to a solution of 1,3-dichloroacetone and the stirring continued for time sufficient to complete the reaction with the formation of the intermediate (3-chloro-2-oxopropyl)thioimidazolium chloride compound which precipitates in the reaction mixture. The latter may then be purified according to conventional procedures.

In the second step, the intermediate compound thus prepared and the sodium salt of a mercaptoheteroaryl compound are caused to react in solution in a solvent such as ethanol or isopropanol. In carrying out the reaction the [(3-chloro 2-oxopropyl)thio]imidazolium salt compound is added to a solution of the sodium salt of the mercapto compound whereupon a precipitate forms immediately which may be recovered and purified, if desired, employing conventional procedures.

The same compound may be obtained by another approach. In this approach, the sodium mercaptoheteroaryl compound is caused to react with one molar portion of 1,3-dichloroacetone to obtain a 3-chloro-2-oxopropyl thio-heteroaryl compound which is then caused to react with an appropriate imidazolinethione.

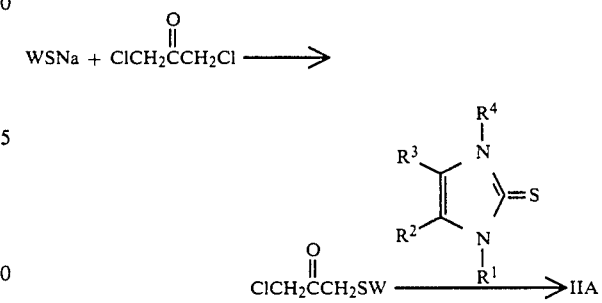

The first step of the reaction is carried out preferably in a solvent mixture of ethanol and ether by adding dropwise a solution of the sodium salt of the mercaptoheteroaryl compound to a solution of the 1,3-dichloroacetone, and stirring the resulting mixture at ambient temperature for several hours to overnight obtain a 1-chloro 3-(heteroarylthio)propanone intermediate in the reaction mixture. The mixture is filtered to remove undesired impurities and then cooled to precipitate the desired intermediate which then may be recovered and purified employing conventional procedures.

The intermediate then is intimately admixed with a solution of the appropriate imidazoline-2-thione at room temperature for from several hours to overnight whereupon a reaction takes place with the formation and precipitation of the desired chloride salt in the reaction mixture. The salt may be recovered and purified in a conventional manner.

The imidazolium salts in which $X^-$ is halide may be converted to salts in which $X^-$ is trifluoromethanesulfonate or other anions by charging an ion-exchange column with the sodium salt of trifluoromethanesulfonate or other desired anion in a conventional manner. Thereafter, the imidazolium halide is charged on the column in a solvent such as methanol and the desired imidazolium salt recovered from the eluate by vaporizing off the solvent.

When the imidazolium salt is an unsymmetrical i.e.. if W is a different imidazolyl group or is a different heteroaryl group, the imidazolium mono salt may be caused to react with an active quaternizing agent.

*IIA + R″Z→IIB*

Alternatively, the bis salt may be obtained by first obtaining a mono salt represented by the formula

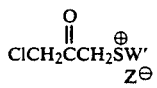

by intimately contacting chloroacetone and WSNa in a solvent such as acetone or methyl ethyl ketone at ambient temperature to obtain a compound represented by the formula

which may be recovered and purified by conventional procedures and then intimately mixing this compound with R"Z in the manner previously described for preparation of salts to obtain the mono quaternary salt of the above formula. The mono quaternary salt then may be caused to react in solution in ethanol or isopropanol with an imidazolinethione to obtain IIB

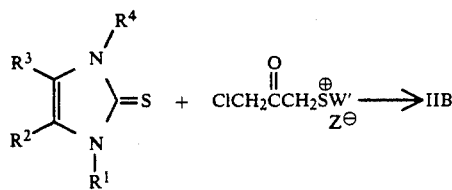

which then may be recovered in a manner previously described.

The usefulness of the compounds as Factor XIIIa inhibitors for enchancing the rate of clot lysis catalyzed by plasminogen activators may be demonstrated first by establishing the inhibitory potencies of the compounds in a Factor XIIIa assay.

The Factor XIIIa inhibitor assay is based on the incorporation of $^{14}C$-putrescine into casein catalyzed by Factor XIIIa. The assay is carried out employing the procedure described in Methods in Enzymology, Vol. 45, Ch 15., pages 177–191 (1976) and using Factor XIII (F XIII) isolated from human plasma. The procedure is summarized briefly and schematically illustrated as follows:

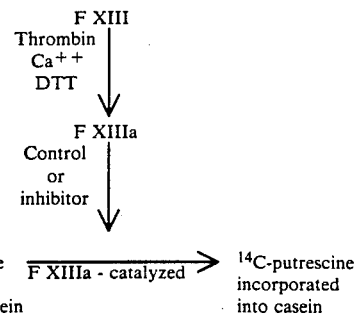

Factor XIII assay mixtures are prepared by adding stepwise, appropriately prepared solutions of thrombin and dithiothreitol (DTT) to a mixture comprising Factor XIII at 140 μg/mL in glycerol/water and tris(hydroxymethyl)aminomethane hydrochloride (Tris.HCl). To a portion of the mixture is added calcium chloride as source of calcium ions required for enzyme activity and to the remaining mixture is added, instead of calcium ions, ethylenediaminetetraacetic acid (EDTA) which serves as a blank for background.

A substrate mixture is prepared from $^{14}C$-putrescine and N,N-dimethylcasein.

The assay tubes and control tubes are charged with the substrate mixture and incubated at 37° C. for 20 minutes Samples are withdrawn from each tube, spotted onto a filter disc which is then immersed in ice cold trichloroacetic acid solution to Precipitate the casein on the filter. The filter is then washed to remove unincorporated or free $^{14}C$-putrescine and after drying is counted for $^{14}C$-putrescine incorporated to casein from which percent activity and/or inhibition can be calculated.

Imidazole compounds showing at least 50 percent activity at $2 \times 10^{-5}$ M in the Factor XIIIa assay are considered to be useful in inhibiting hard clot formation or especially in supplementing fibrinolysis by plasminogen activator.

The imidazoles and imidazolium salts seen in Table I are representatives of compounds having $IC_{50}$ at concentrations below $2 \times 10^{-5}$ M. Also seen in Table I are the properties of the various compounds.

TABLE I

| R¹ | R² | R³ | R⁴ | X⁻ Anion or Salt | W | W' | Z⁻ or Salt | M.P. °C. |
|---|---|---|---|---|---|---|---|---|
| CH₃ | H | H | CH₃ | I⁻ | 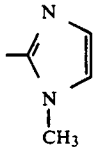 | — | — | 135–137° |
| CH₃ | H | H | — | — | 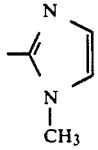 | — | — | 194° |

TABLE I-continued

| R¹ | R² | R³ | R⁴ | X⁻ Anion or Salt | W | W' | Z⁻ or Salt | M.P. °C. |
|---|---|---|---|---|---|---|---|---|
| CH₃ | H | H | CH₃ | Cl⁻ | — | 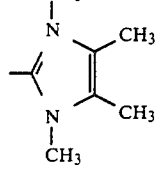 | Cl⁻ | — |
| CH₃ | CH₃ | CH₃ | CH₃ | Cl⁻ | — | 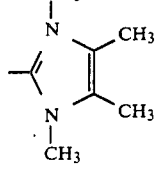 | Cl⁻ | 89–103° |
| CH₃ | H | H | CH₃ | Cl⁻ | 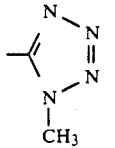 | — | — | 196–197° |
| CH₃ | CH₃ | CH₃ | CH₃ | Cl⁻ | 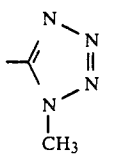 | — | — | 145–146° |
| CH₃ | —(CH₃)₄— | | CH₃ | Cl⁻ | 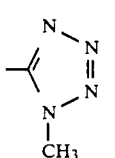 | — | — | 128–130° (dec) |

For use in facilitating or supplementing fibrinolytic therapy, the imidazole compound may be administered in a pre- or post-lytic state alone or in combination therapy with a plasminogen activator, with a platelet aggregation inhibitor or with natural and synthetic anticoagulants.

The process for facilitating or supplementing fibrinolytic therapy in prothrombic patients comprises administering a therapeutic dose of an imidazole compound in an amount to provide between 1.4–140 mg/kg/day while considering patient's health, weight, age and other factors which influence drug response. The drug may be administered per os or by injection, and if by injection, either by single injection, multiple injections or continuous infusion.

In the preferred process of the present invention, the imidazole compound is administered with a plasminogen activator in a combination therapy. When combination therapy is employed, it is preferable to administer the Factor XIIIa inhibitor imidazole compound first in a single bolus and thereafter to administer the plasminogen activator by continuous infusion. However, both may be administered simultaneously as a continuous infusate. Under certain circumstances it may be desirable to administer the imidazole compound subsequent to the administration of the plasminogen activator. It is intended that the method of the present invention embrace concurrent administration as well as sequential administration, in any order.

When the Factor XIIIa inhibitor imidazole compound and plasminogen activator are employed in a combination therapy, it is most desirable to use the plasminogen activator in the dose range of about 500 to 10,000 I.U. kg/minute for from about 30 to 180 minutes and the imidazole compound in the range of 1 μg–100 μg/kg/minute for a day (1440 minutes).

When the imidazole compound is to be used with a platelet aggregation inhibitor in combination therapy, the dose range for platelet aggregation inhibitor depends on the nature of the inhibitor. When the platelet aggregation inhibitor is aspirin, the aspirin may be employed at a dose of 25–325 mg twice a day. When the platelet aggregation inhibitor compound is dipyridamole, the dipyridamole may be employed at a dose of 25–100 mg four times a day. When the platelet aggregation inhibitor is a semi-synthetic peptide such as "Echistatin" or "Bitistatin", the peptide may be administered in a dose range of 0.1 to 1 nanomole/kg/min. for from 30 to 180 minutes. In each case, the imidazole compound may be employed in the range of 1–100 μg/kg/min. for a day. The administration may be carried out simultaneously or sequentially in any order as in the procedure for administration with plasminogen activators.

When the imidazole compound is to be used with heparin, heparin may be administered at doses of 4000 to 8000 units per 4 hours and the imidazole compound in the range of 1 μg-100 μg/kg/minute for a day. When it is to be used with coumarin drugs, these drugs are administered orally at doses of 10 to 15 mg/kg/day and the imidazole compound administered by infusion at a rate of 1 μg/kg/minute to 100 μg/kg/minute for a day.

Compositions to be employed in the practice of the present invention whether parenteral, oral or suppository compositions comprises an imidazole compound in a pharmaceutically acceptable carrier.

Parenteral compositions comprise the imidazole compound in sterile physiologically acceptable media such as physiological saline. Such compositions may also contain other ingredients for purposes such as for aiding solubility or for preservation or the like, said ingredients being those acceptable for intravenous administration. The compositions may be prepared as concentrate compositions and lyophilized and then diluted to the appropriate treating composition immediately prior to administration. A therapeutic composition as a unitary dose form may contain from 100 mg to 10 grams of imidazole compound. Compositions suitable in the preferred practice of the present invention of co-administering plasminogen activator and Factor XIIa inhibitor compound may about 58 million I.U. of tissue plasminogen activator (tPA) or 1.5 million I.U. of streptokinase and from 100 mg to 10 grams of the imidazole compound.

Oral compositions also may be prepared with the active ingredient in admixture with a pharmaceutically acceptable carrier. Suitable carriers for liquid compostions include water, glycols, oils, alcohols, flavoring agents, preservatives, coloring agents and the like; for solid preparations, carriers include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

Suppository compositions may be prepared with ointments, Jellies, carbowax, polyethylene, sorbitan monostearate, polyethylene glycol, cocoa butter, and other conventional carriers.

The preparation of the imidazole compounds suitable for inhibiting transglutaminase enzymes, particularly Factor XIIIa, and compositions suitable for carrying out the process of the present invention are illustrated by the following examples but are not to be construed as limiting.

The preparation of the imidazole compounds suitable for inhibiting transglutaminase enzymes, particularly Factor XIIIa, and compositions suitable for carrying out the process of the present invention are illustrated by the following examples but are not to be construed as limiting.

EXAMPLE I 1,3-Dimethyl-2-{[3-([1-methyl-1H-imidazol-2-yl]thio)-2-oxopropyl]thio}-1H-imidazolium chloride

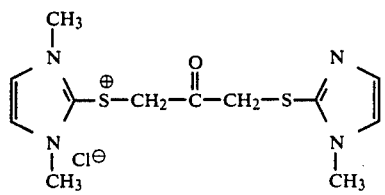

A.

1,3-Bis[(1-methyl-1H-imidazol-2-yl)thio]-2-propanone

To an ice-cooled solution of 2.28 g (0.02 mol) of 2-mercapto-1-methylimidazole and 2.50 g (0.025 mol) of triethylamine in 30 mL of acetone was added a solution of 1.27 g (0.01 mmol) of 1,3-dichloroacetone in 10 mL of acetone dropwise over 40 minutes. After about 2 hours, the ice bath was removed and the mixture was stirred at room temperature for 78 hours. At the end of this time, the triethylammonium chloride was removed by filtration and the filtrate was evaporated in vacuo and the residue was dissolved in $CH_2Cl_2$. This solution was washed with 5% sodium hydroxide solution and water, and dried over $MgSO_4$. Evaporation of the $CH_2Cl_2$ gave a dark brown oil that was purified by flash chromatography on silica gel using 2.5% methanol in $CH_2Cl_2$ as an eluant to obtain 1.0 g of 1,3-Bis[(1-methyl-1H-imidazol-2-yl)thio]-2-propanone as an oil.

B.

1,3-Dimethyl-2-{[(1-methyl-1H-imidazol-2-yl]thio)-2-oxopropyl]thio)}-1H-imidazolium iodide 2.2 grams of methyl iodide was added and intimately contacted with a solution of the oil (1.0 gram) obtained above in 15 mL of acetone whereupon a precipitate of the methiodide salt formed in the reaction mixture. The latter was recovered by filtration and was found to have a melting point of 135-137° C.

C.

1,3-Dimethyl-2{[3-([1-methyl-1H-imidazol-2-yl]thio)-2-oxopropyl]thio}-1H-imidazolium chloride The methiodide salt was dissolved in warm water and placed on a Dowex-1 ($Cl^-$) ion exchange column. The column was washed with water to obtain the corresponding chloride salt in the eluate. The salt was crystallized from isopropyl alcohol-hexane to obtain 1,3-dimethyl-2-{[3-([1-methyl-1H-imidazol-2yl]thio)-2-oxopropyl]}-1H-imidazolium chloride, m.p. 146-148° C.

Anal. Calcd for $C_{12}H_{17}ClN_4OS_2$: C, 43.30; H, 5.15; N, 16.83; Cl, 10.65. Found: C, 43.07; H, 5.06; N, 16.52; Cl, 10.53.

15

EXAMPLE II 1,3-Dimethyl2-({3-[(1-methyl-1H-tetrazol-5-yl)thio]-2-oxopropyl}thio)-1H-imidazolium chloride

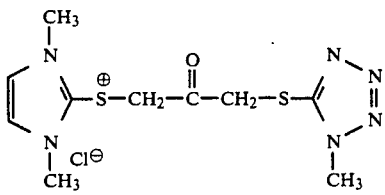

A.
1,3-Dimethyl-2-[(3-chloro-2-oxopropyl)-thio]-1H-imidazolium chloride

A solution of 1.01 g (0.0079 mol) of 1,3-dimethylimidazolin-2-thione (prepared by the procedure Of B.L. Benac et al, Org. Syn. 64, 92 (1985) in 40 mL of acetone was added dropwise to a solution of 1.0 g (0.0079 mol) of 1,3-dichloropropanone in 50 mL of acetone over 2 hours. The resulting solution was stirred at room temperature for 18 hours whereupon a precipitate formed. The latter was removed by filtration and dried to obtain 1.76 g (87%) of 1,3-dimethyl-2-[(3-chloro-2-oxopropyl)thio]-1H-imidazolium chloride, m.p. 157–158° C.

Anal. Calcd for $C_{12}H_{20}Cl_2N_4OS_2$: C, 37.65; H, 4.74; N, 10.98; Found: C, 37.45; H, 4.83; N, 11.02.

B.
1,3-Dimethyl-2-({3-[(1-methyl-1H-tetrazol-5-yl)thio]-2-oxopropyl}thio)-1H-imidazolium chloride To a solution of 0.271 g (0.00196 mol) of 5-mercapto-1-methyltetrazole sodium salt hydrate in 30 mL of absolute ethanol was added 0.50 g (0.0020 mol) of 1,3-dimethyl-2-[(3-chloro-2-oxopropyl)thio]-1H-imidazolium chloride whereupon a white precipitate formed immediately. The precipitate was removed by filtration and was recrystallized from ethanol to obtain the desired 1,3-dimethyl-2-({3-[(1-methyl-1H-tetrazol-5-yl)thio]-2-oxopropyl}thio)-1H-imidazolium chloride, m.p. 196–197° C.

Anal. Calcd for $C_{10}H_{15}ClN_6OS_2$: C, 35.87; H, 4.51; N, 24.41; Found: C, 35.83; H, 4.62; N, 25.10.

EXAMPLE III 1,3,4,5-Tetramethyl-2-({3-[(1-methyl-1H-tetrazol-5-yl)thio]-2-oxopropyl}thio)-1H-imidazolium chloride

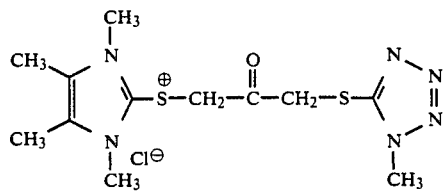

A. 1-Chloro-3-(1-methyltetrazolyl-5-thio)-2-propanone

A solution of 1.38 g (0.001 mol) of 5-mercapto-1-methyl-tetrazole sodium salt hydrate in 10 mL of ethanol was added dropwise to a solution of 6.5 g (0.005 mol) of 1,3-dichloroacetone in 15 mL of ether and 10 mL of absolute ethanol.

The resulting mixture was stirred at room temperature for 3 hours; thereafter the solution was filtered and then was cooled whereupon a precipitate formed. It was removed by filtration, triturated with ether, and collected to obtain 0.33 g of 1-chloro-3-(1-methyl-tetrazolyl-5-thio)-2-propanone.

B.
1,3,4,5-Tetramethyl-2-({3-[(1-methyl-1H-tetrazol-5-yl)thio]-2-oxopropyl}-thio)-1H-imidazolium chloride A solution of 0.330 g (0.00169 mol) of the compound prepared in Part A and 0.249 g (0.00159 mol) of 1,3,4,5-tetramethylimidazoline-2-thione in 10 mL of acetone was stirred overnight at room temperature whereupon a product was found to have precipitated.

It was collected by filtration and was recrystallized from isopropyl alcohol-acetone-hexane to obtain 0.27 g of the desired 1,3,4,5-tetramethyl-2-({3-[(1-methyl-1H-tetrazol-5-yl)thio]-2-oxopropyl}thio)-1H-imidazolium chloride, m.p. 115–117°.

Anal. Calcd for $C_{12}H_{19}ClN_6OS_2$: C, 39.71; H, 5.28; N, 23.16; Found: C, 39.54; H, 5.11; N, 23.12.

EXAMPLE IV 2,2'-[(2-Oxo-1,3-propane-diyl)bis(thio)]bis(1,3,4,5-tetramethyl)-1H-imidazolium dichloride

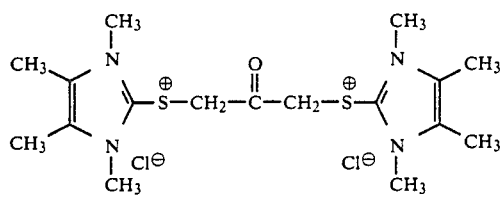

To 0.127 g (0.001 mol) of 1,3-dichloro-2-propane was added to a solution of 0.315 g (0.002 mol) of 1,3,4,5-tetramethylimidazoline-2-thione in 5 ml of acetone. The solution was stirred overnight at room temperature whereupon solids precipitated in the reaction mixture. The solids were removed by filtration and washed with acetone to obtain the desired 2,2'-[(2-oxo-1,3--propanedioyl)bis(thio)]bis (1,3,4,5-tetramethyl)-1H-imidazolium dichloride, m.p. 89–103° .

Anal. Calcd for $C_{17}H_{28}Cl_2N_4OS_2$: C, 45.50; H, 7.04; N, 12.19; Cl, 16.20. Found: C, 45.16; H, 6.56; N, 12.39; Cl, 15.69.

EXAMPLE V 2-({(3-[(1,3-dimethyl-1H-imidazolium-2-yl)thio]-2-oxopropyl)thio)-1,3,4,5-tetramethyl-1H-imidazolium dichloride

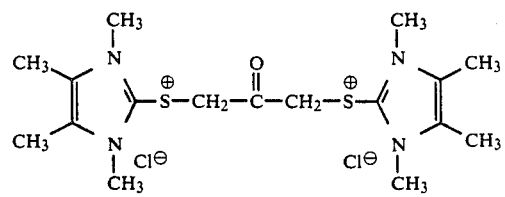

To 0.255 g (0.001 mole) of 1,3-dimethyl-2-[(3-chloro-2-oxopropyl)thio]-1H-imidazolium chloride was added a solution of 0.156 g (0.001 mol) of 1,3,4,5-tetramethylimidazoline-2-thione in 5 mL of ethanol and the reaction mixture was stirred for 3 hours at ambient temperature. At the end of this period, the solvent was evaporated and the residue was crystallized from isopropyl alcohol-acetonehexane to obtain the desired 2-{(3-[(1,3-dimethyl-1H-imidazolium-2-yl)thio]-2-oxopropyl)thio}- 1,3,4,5-tetramethyl-1H-imidazolium dichloride compound as a hygroscopic solid.

EXAMPLE VI

In operations carried out in a manner similar to that described in Example I, the following compounds are prepared

| $R^1$ | $R^2$ | $R^3$ | $R^4$ | Anion ($X^-$) or Salt (HX) | W | W' | ANION ($Z^-$) or Salt (HZ) |
|---|---|---|---|---|---|---|---|
| $-CH_3$ | $-CH_3$ | H | $-CH_3$ | $CF_3SO_3^-$ | 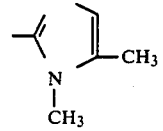 | — | — |
| $-CH_3$ | $-C_3H_7$ | $-C_3H_7$ | $-CH_3$ | $CF_3SO_3^-$ | 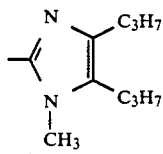 | — | — |
| $-CH_3$ | $-CH_3$ | $-C_3H_7$ | $-CH_3$ | $I^-$ | 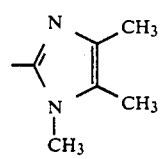 | — | — |
| $-CH_2C_6H_5$ | $-(CH_2)_4-$ | | $-CH_2C_6H_5$ | $Cl^-$ | — | 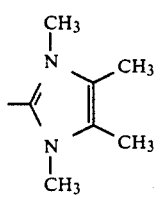 | $Cl^-$ |
| $-CH_2(CH_3)_3$ | $-C_6H_5$ | H | $CH_2(CH_3)_2$ | $Cl^-$ | — | 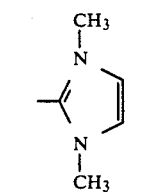 | $Cl^-$ |
| $-C_2H_5$ | $-Cl$ | H | $C_2H_5$ | $Cl^-$ | — | 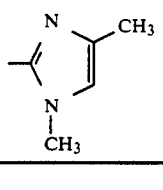 | $Cl^-$ |

Anal. Calcd for $C_{15}H_{24}Cl_2N_4OS_2 \cdot 1.4\ H_2O \cdot 0.1 C_3H_8O$: C, 41.31; H, 6.36; N, 12.99; Cl, 15.80. Found C, 41.56; H, 6.29; N, 12.88; Cl, 16.04.

EXAMPLE VII

In operations carried out in a manner similar to that described in Example II the following compounds may be prepared

| $R^1$ | $R^2$ | $R^3$ | $R^4$ | Anion (X) or Salt (HX) | W | W' | ANION (Z) or Salt (HZ) |
|---|---|---|---|---|---|---|---|
| $-CH_3$ | $-CH_3$ | H | $-CH_3$ | $Cl^-$ | 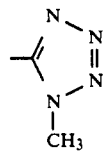 | — | — |

-continued

| R¹ | R² | R³ | R⁴ | Anion (X) or Salt (HX) | W | W' | ANION (Z) or Salt (HZ) |
|---|---|---|---|---|---|---|---|
| —CH₃ | —C₃H₇ | C₃H₇ | —CH₃ | Cl⁻ | 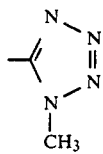 | — | — |
| —CH₃ | Cl | Cl | —CH₂C₆H₅ | Br⁻ | — | 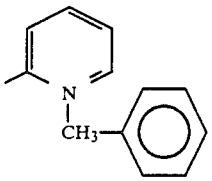 | Br⁻ |
| —CH₂C₆H₅ | —(CH₂)₆— | | —CH₂C₆H₅ | Br⁻ | — | 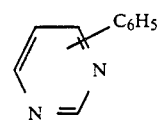 | Br⁻ |
| —CH₂CH₂C₆H₅ | 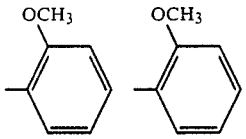 |  | CH₂CH₂C₆H₅ | —CF₃SO₃⁻ | — | 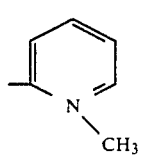 | I⁻ |
| —CH₂C₆H₄OCH₃(P) | —C₆H₅ | —Br | CH₂C₆H₄OCH₃(P) | CF₃SO₃⁻ | — | 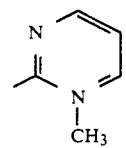 | CF₃SO₃⁻ |

EXAMPLE VIII

Parenteral Composition

One liter of a Parenteral composition comprising one of the foregoing compounds may be prepared from the following formulation:

| | Grams |
|---|---|
| Imidazolium compound | 5.0 |
| Polysorbate 80 | 2.0 |
| Sodium Chloride | 9.0 |
| Sodium carboxymethyl cellulose | 10.0 |
| Methyl paraben | 1.8 |
| Propyl paraben | 0.2 |
| Water, USP | q.s. to 1 liter |

The parabens, sodium chloride and carboxymethylcellulose are dissolved in one-half the total volume of water by heating to 95° C. to obtain a solution which is then filtered and autoclaved. The polysorbate is dissolved in one-third of the total volume of water and the resulting solution also filtered and autoclaved. Sterile active ingredient is added to the second solution and the mixture passed through a sterile colloid mill to obtain a suspension of active ingredient. The first solution is added to the suspension with stirring then U.S.P. water added to 1 liter. Sterile vials are filled with the suspension while stirring.

EXAMPLE IX

Oral Composition 5000 compressed tablets each containing as active ingredient 100 milligrams of one of the foregoing compounds, may be prepared from the following formulation:

| | Grams |
|---|---|
| Imidazolium compound | 500 |
| Starch | 700 |
| Dibasic calcium phosphate hydrous | 5000 |
| Calcium stearate | 25 |

The ingredients are finely powdered, mixed well and then granulated with 10 percent starch paste. The granulation is dried and compressed into tablets using starch as a disintegrant and calcium stearate as lubricant.

Preparation of the Starting Materials

A. 2-Mercaptoimidazole

The 2-mercaptoimidazoles may be obtained by a reaction between an appropriate acyloin and mono-substituted urea according to the following equation:

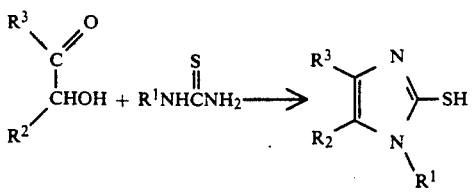

The reaction may be carried out by fusing the reactants or by refluxing the components in hexano-1-1 as more fully described by Nuhn P. et. al., J. fur praktische Chemie, 312, 90 (1970) for the fusion method and by KJellin, G. et. al., Acta Chemica Scandinavica, 23, 2879 (1969) for the method where the α-hydroxyketones and N-alkylthioureas are refluxed in 1-hexanol with a water separator. The teachings of the foregoing articles on the preparation of the starting 2-mercaptoimidazoles are incorporated by reference.

The acyloins may be prepared in any manner within the knowledge of those skilled in the art.

B. 1,3-Disubstituted-imidazoline-2-thione 1,3-disubstituted-imidazoline-2-thione may be obtained by the reaction between an α-hydroxyketone and di-substituted thiourea according to the equation

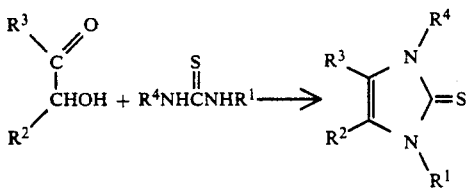

The reactants may be intimately contacted in the manner described by Kjellin et al in the above cited Acta Chemica Scandinavica article and also may be prepared by the method of J. Kisler et al, Can. J. Chem. 57, 813(1979), which teachings are incorporated by reference.

What is claimed is:

1. an imidazolium salt represented by the formula

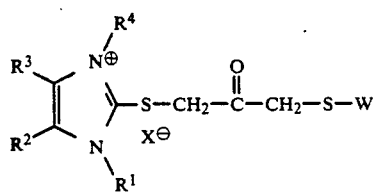 (A)

or

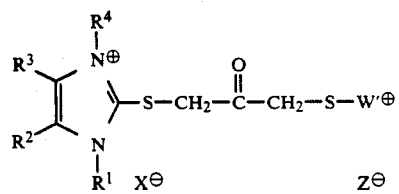 (B)

wherein $R^1$ is lower alkyl or $ArC_nH_{2n}$— wherein Ar is phenyl, (lower alkyl)phenyl, or halophenyl and n is 1 to 3

$R^2$ is hydrogen, lower alkyl, phenyl or substituted phenyl containing from 1 to 3 substituents selected from lower alkyl, lower alkoxy, halo and hydroxy;

$R^3$ is hdyrogen, lower alkyl, halo, phenyl or substituted phenyl containing from 1 to 3 substituents selected from lower alkyl, lower alkoxy, halo and hydroxy;

$R^2$ and $R^3$ taken together is alkylene of from 3 to 10 carbon atoms;

$R^4$ is lower alkyl or aralkyl;

W is

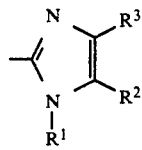

where $R^1$, $R^2$, and $R^3$ are as previously defined, or

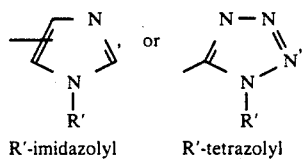

R'-imidazolyl    R'-tetrazolyl wherein R' is lower alkyl or $ArC_nH_{2n}$— wherein Ar is phenyl, (lower alkyl)phenyl, (lower alkoxy)phenyl or halophenyl and n is 1–3;

W' is

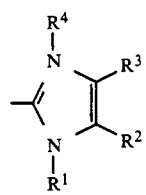

where $R^1$, $R^2$, and $R^3$ are as previously defined, or

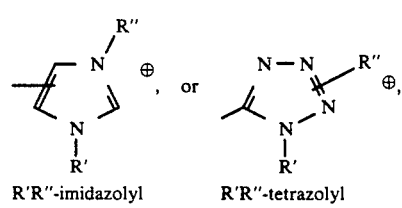

R'R''-imidazolyl    R'R''-tetrazolyl wherein R' and R'' independently are lower alkyl or $ArC_nH_{2n}$ wherein Ar is phenyl, (lower alkyl)phenyl, (lower alkoxy)phenyl) or halophenyl and n is 1–3;

X is an anion of a pharmaceutically acceptable salt;

Z is an anion of a pharmaceutically acceptable salt.

2. A compound according to claim 1 in which W or W' is an imidazole nucleus.

3. A compound according to claim 1 in which W or W' is a tetrazole nucleus.

4. A compound according to claim 1 which is 1,3-dimethyl-2-{[3-([1-methyl-1H-imidazol-2-yl]thio)-2-oxopropyl]thio}-1H-imidazolium chloride.

5. A compound according to claim 1 which is 1,3-dimethyl-2-{3-[(1-methyl-1H-tetrazol-5-yl)thio]-2-oxopropyl}thio)-1H-imidazolium chloride.

6. A compound according to claim 1 which is 1,3,4,5-tetramethyl-2-({3-[(1-methyl-1H-tetrazol-5-yl)-thio]-2-oxopropyl}thio)-1H-imidazolium chloride.

7. A compound according to claim 1 which is 2,2'-[(2-oxo-1,3-propane-diyl)bis(thio)-bis(1,3,4,5-tetramethyl)-1H-imidazolium dichloride.

8. A compound according to claim 1 which is 2-{(3-[(1,3-dimethyl-1H-imidazolium-2-yl)thio]-2-oxopropyl)thio}-1,3,4,5-tetramethyl-1H-imidazolium dichloride.

9. A composition suitable for thrombolytic therapy in inhibiting or combatting thrombosis or for supplementing fibrinolytic therapy comprising an amount of an imidazole compound of claim 1 in a pharmaceutically acceptable carrier.

10. A composition according to claim 9 in unit dose form wherein the imidazole compound is present in amount of 100 mg to 10 grams.

11. A method for inhibiting hard clot formation, or supplementing fibrinolytic therapy comprising administering to a patient in need of such treatment an imidazole compound of claim 1 in an amount effective for inhibiting hard clot formation, or supplementing fibrinolytic therapy.

12. A method according to claim 11 wherein the imdazole compound is administered to provide about 1–100 µg/kg/minute for one day.

* * * * *